(12) United States Patent
Hecker

(10) Patent No.: US 7,733,483 B2
(45) Date of Patent: Jun. 8, 2010

(54) METHOD FOR ASCERTAINING THE ORIENTATION OF MOLECULES IN BIOLOGICAL SPECIMENS

(75) Inventor: Andreas Hecker, Asslar (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 1084 days.

(21) Appl. No.: 11/374,287

(22) Filed: Apr. 20, 2006

(65) Prior Publication Data

US 2006/0292632 A1 Dec. 28, 2006

(30) Foreign Application Priority Data

May 19, 2005 (DE) .................. 10 2005 023 768

(51) Int. Cl.
*G01J 3/30* (2006.01)
(52) U.S. Cl. ..................................... 356/318
(58) Field of Classification Search ............ 356/318
See application file for complete search history.

(56) References Cited

U.S. PATENT DOCUMENTS 7,518,764 B2 * 4/2009 Osborne et al. ............ 358/481

2002/0097489 A1  7/2002  Kawano et al.
2004/0001253 A1  1/2004  Abe et al.

FOREIGN PATENT DOCUMENTS

| DE | 101 08 796 A1 | 9/2002 |
|----|---|---|
| DE | 101 43 481 A1 | 3/2003 |
| DE | 102 17 098 A1 | 11/2003 |
| DE | 102 29 935 A1 | 1/2004 |
| WO | WO-2005/031427 A1 | 4/2005 |
| WO | WO-2005/031432 A1 | 4/2005 |

\* cited by examiner

*Primary Examiner*—Tarifur Chowdhury
*Assistant Examiner*—Abdullahi Nur
(74) *Attorney, Agent, or Firm*—Leydig, Voit & Mayer, Ltd.

(57) ABSTRACT

A method of ascertaining the orientation of molecules in a biological specimen by total internal reflection includes focusing illuminating light through an objective in different positions in a plane of a pupil of the objective so as to generate a plurality of respective differently oriented evanescent fields in the specimen. Respective different fluorescence intensities resulting from the differently oriented evanescent fields are correlated with respective different orientations of molecules in the specimen.

20 Claims, 2 Drawing Sheets

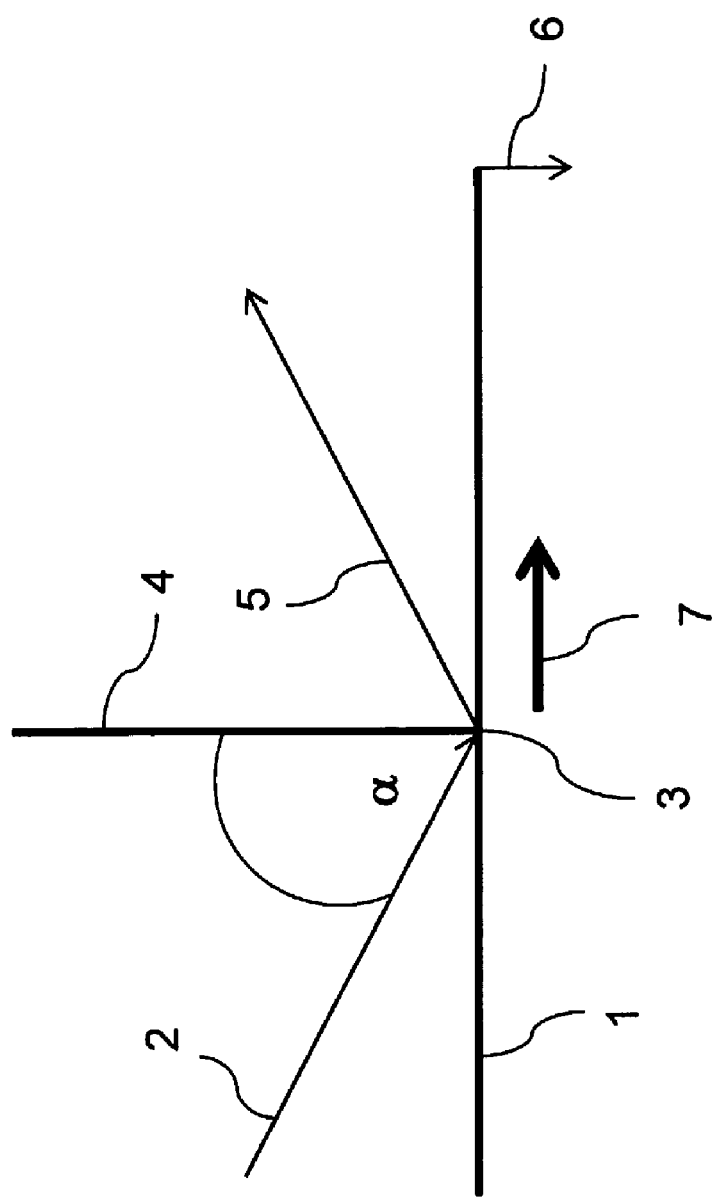

METHOD FOR ASCERTAINING THE ORIENTATION OF MOLECULES IN BIOLOGICAL SPECIMENS

CROSS REFERENCE TO RELATED APPLICATIONS

This application claims priority under USC §119(a)-(d) to German patent application 10 2005 023 768.1, filed May 19, 2005, the entire subject matter of which is hereby incorporated by reference herein.

FIELD OF THE INVENTION

The present invention relates to a method for ascertaining the orientation of molecules in biological specimens, in particular in cells, utilizing total internal reflection microscopy.

BACKGROUND OF THE INVENTION

In total internal reflection microscope, the refractive behavior of light when transitioning from an optically denser to an optically less dense medium is utilized. For the transition from coverslip (n1=1.518) to water (n2=1.33), for example, the result is a critical angle of 61°, or the total reflection angle. Under total reflection conditions (angle=61°), a standing evanescent wave forms in the medium having the lower refractive index. The intensity of this wave decreases exponentially with distance from the interface. As a result of this, fluorophores located farther from the interface are not excited. The background fluorescence is considerably reduced, thereby improving image contrast and at the same time greatly raising resolution. A prerequisite for utilization of the phenomenon described above is a sufficiently large difference in refractive index between the coverslip and medium.

US 2002/0097489 A1 discloses a microscope with evanescent illumination of a specimen. The microscope contains a white-light source whose light is coupled, for evanescent illumination, via a slit stop through the microscope objective into the specimen slide carrying a specimen. The illuminating light propagates in the specimen slide by total internal reflection, illumination of the specimen occurring only in the region of the evanescent field projecting out of the specimen slide. Microscopes of this kind are known as TIRFM (total internal reflection fluorescent microscopes).

Because the evanescent field projects only approximately 100 nm into the specimen, the Z resolution of TIRF microscopes is extraordinarily good.

DE 101 08 796 A1 discloses a high-aperture objective, in particular for TIRF applications. The objective is made up of a first lens having positive refractive power and a second lens having negative refractive power, the focal length ratio between the two lenses being in the range from −0.4 to −0.1, and the total refractive power being greater than zero. The objective furthermore contains two positive lenses whose ratio of diameter to focal length is greater than 0.3 and less than 0.6. The objective furthermore contains a negative lens and a converging lens; the negative lens faces toward the front group and the focal length ratio of the negative lens and the converging lens is between −0.5 and −2.

DE 102 17 098 A1 discloses an incident illumination arrangement for TIRF microscopy. The incident illumination arrangement contains an illumination source that, in operation, emits a polarized illumination ray bundle that propagates at an angle to the optical axis, and a deflection device that deflects the illumination ray bundle and couples it into the objective parallel to the optical axis. In this incident illumination arrangement, provision is made for the illumination ray bundle emitted by the illumination source to have s and p polarization directions with a phase difference, and for the deflection device to reflect the illumination ray bundle x times, where x=((n×180°−d)/60°).

DE 101 43 481 A1 likewise discloses a microscope for total internal reflection microscopy (TIRM). The microscope comprises a microscope housing and an objective. The illuminating light proceeding from an illumination device can be coupled in via an adapter insertable into the microscope housing.

US 2004/0001253 A1 discloses a microscope having an optical illumination system that allows an easy switchover between evanescent illumination and reflected illumination. The illumination system contains a laser light source whose light is coupled into an optical fiber. Also provided is an outcoupling optical system that focuses the light emerging from the fiber into a rear focal point of the microscope objective. The optical fiber is displaceable in a plane perpendicular to the optical axis of the microscope objective.

DE 102 29 935 A1 discloses a device for coupling light into a microscope in which, in the field diaphragm plane, laser light is directed onto the sample through a light-guiding fiber incoupling system embodied as a slider. This is suitable in particular for the TIRF method.

In the investigation of biological specimens in particular, especially the investigation of the molecular structure of cells, there exists a need to ascertain the orientation of the molecules or dipoles in the specimen. It would be particularly advantageous if such orientations could be ascertained using apparatuses that are already in use in any case for investigation of the biological specimens.

SUMMARY OF THE INVENTION

It is therefore an object of the present invention to provide a method for ascertaining the orientation of molecules in biological specimens, in particular in cells, which uses equipment that is already in use in any case for the investigation of biological specimens.

The present invention provides a method for ascertaining the orientation of molecules in biological specimens, in particular in cells. The method utilizes total internal reflection microscopy, illuminating light being focused through an objective in the plane of the objective pupil, differently oriented evanescent fields being generated in the specimen by the illumination of different positions in the objective pupil, and different fluorescence intensities resulting therefrom being correlated with different orientations of the molecules in the specimen.

What has been recognized according to the present invention is firstly that total internal reflection microscope is also suitable for ascertaining the orientation of molecules in biological specimens. It is essential that in the context of this particular type of microscopy, a microscope objective be illuminated in evanescent fashion by point-like illumination of the objective exit pupil. This is accomplished by focusing illuminating light, through an objective, in the plane of the objective pupil. In the context of this method, different positions in the objective pupil are traveled to and illuminated, resulting in a very particular situation in terms of the evanescent field produced in the specimen, i.e. in terms of the propagation direction of the evanescent field relative to the respective molecules in the specimen. The light beam incident onto the interface results in a corresponding propagation direction of the evanescent field in the plane constituted by the incident light beam and the line perpendicular to the interface. The evanescent wave produced in the specimen acquires a specific orientation corresponding to the position of the illuminating light in the objective pupil and also corresponding to the angle of incidence of the light, thereby yielding a propagation direction of the evanescent field relative to the specimen being investigated and thus relative to the molecules present therein. The particular type of illumination, namely by means of an evanescent field having a defined propagation direction, results in different fluorescence intensities. These different intensities are correlated with the respective (different) orientations of the molecules or dipoles in the specimen, so that the orientation of the molecules can be identified in accordance with the molecules' "response" by way of the fluorescence intensities.

Be it noted at this juncture that in order to ascertain the orientation of molecules in biological specimens by means of total internal reflection microscopy, it is desireable to focus illuminating light on different positions in the objective pupil, in order thereby to initiate differently oriented evanescent fields. It is then possible to draw conclusions as to the molecules' orientation by comparing the intensity of the fluorescent light.

A laser light source is preferably used to illuminate the specimen. A usual white-light source, for example with a slit stop, can likewise be used.

It is additionally advantageous if, for the illumination of different positions in the objective pupil, in particular of any desired positions, the light beam is positioned by means of an adjusting device that acts two-dimensionally. Adjusting devices such as those known, for example, from WO 2005/031427 A1 or from WO 2005/031432 A1 (considered separately) can be used. Be it noted once again that what is of interest here is the illumination of different positions in the objective pupil, thus allowing differently oriented evanescent fields to be generated in the specimen. Any desired points in the objective pupil can be illuminated with the aid of an adjusting device that acts two-dimensionally, so that an adjusting device of this kind meets the requirements for ascertaining the orientation of molecules in biological specimens. In the case where a laser light source is used, the laser light beam can be positioned as desired in the objective pupil by means of the adjusting device, so that the orientation of the molecules inside the cells can in turn be resolved and correspondingly displayed in accordance with the statements made above.

Different positions in the objective pupil are illuminated with the illuminating light, the respective position of the illuminating light correspondingly producing a specific relative orientation of the resulting evanescent field with reference to the respective molecule orientation. Interactions between the cell's constituents (molecules or dipoles) and the propagation direction of the evanescent field thus occur because of the position of the constituent within the biological environment.

Specifically, different orientations between the propagation direction of the evanescent field and the orientation of the molecules in the specimen produce different interaction cross sections, which in turn result in different fluorescence intensities. The respective positions or orientations of the molecules can be deduced from the different intensities.

Advantageously, the specimen is illuminated in evanescent fashion in a preferably predeterminable sequence of pupil positions. This in turn yields a sequence of evanescent fields having different propagation directions, from which images can be generated based on the resulting fluorescence or fluorescence intensity. The orientation of a molecule or of the molecules present in the specimen is determined from the changes in fluorescence intensity within the sequence.

In the context of evanescent illumination of the specimen in a specific sequence, it is additionally advantageous if the sequence of pupil positions is selected in such a way that evanescent fields resulting therefrom are oriented with respect to one another at a predeterminable angle, specifically to allow a limitation in terms of the possible orientation of the molecules to be performed. For example, the sequence of pupil positions can be selected in such a way that evanescent fields resulting therefrom are first oriented orthogonally to one another, to allow a consideration in terms of limit values regarding the orientation of the molecules. This takes into account the particular situation, by way of example, in which a molecule or dipole fluoresces at high intensity when an evanescent field strikes the molecule at a specific angle, whereas with an evanescent field orientation rotated or offset 90 degrees, little further fluorescence, or none at all, then occurs.

For an unequivocal determination of the orientation of a molecule, in particular of a dipole, it is further advantageous if its emission behavior in the context of evanescent fields oriented differently with respect to the molecule is presupposed to be known, so that the orientation of the molecule is deducible from the different intensities corresponding to the sequence of positions of the illuminating light in the objective pupil.

BRIEF DESCRIPTION OF THE DRAWINGS

There are various ways of advantageously embodying and refining the teaching of the present invention. The present invention is elaborated upon below based on exemplary embodiments with reference to the drawings. In the drawings:

FIG. 1 schematically depicts the principle of evanescent illumination in the case of total reflection.

DETAILED DESCRIPTION OF THE INVENTION

Figure 2B:
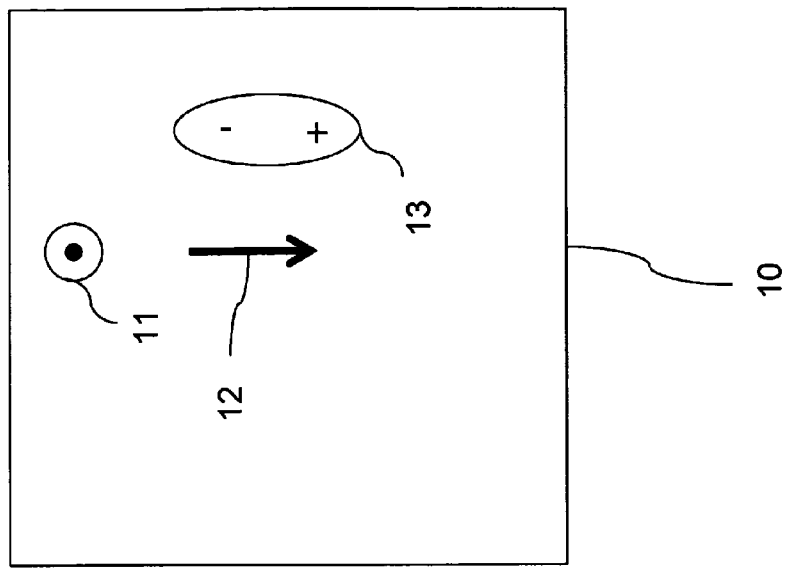
FIGS. 2a and 2b are schematic views of a specimen, the evanescent field propagating with a different orientation with respect to a molecule or dipole of a biological specimen in accordance with the position of the illuminating light in the objective pupil.

FIG. 1 shows the principle of evanescent illumination in the context of total reflection. The specimen to be illuminated is depicted only by its interface 1. A laser light beam 2, constituting illuminating light, is focused in the plane of the objective pupil, resulting in a particular position of the focused illuminating light on the specimen or interface 3. Laser light beam 2 strikes the specimen at a specific angle α to the perpendicular 4. The incident laser light beam 2 is totally reflected, as depicted by the reflected laser light beam 5.

In accordance with the evanescent illumination principle, an evanescent field symbolized by an arrow 6 penetrates into the specimen. Arrow 7 symbolizes the propagation direction of the evanescent field.

Figure 2A:
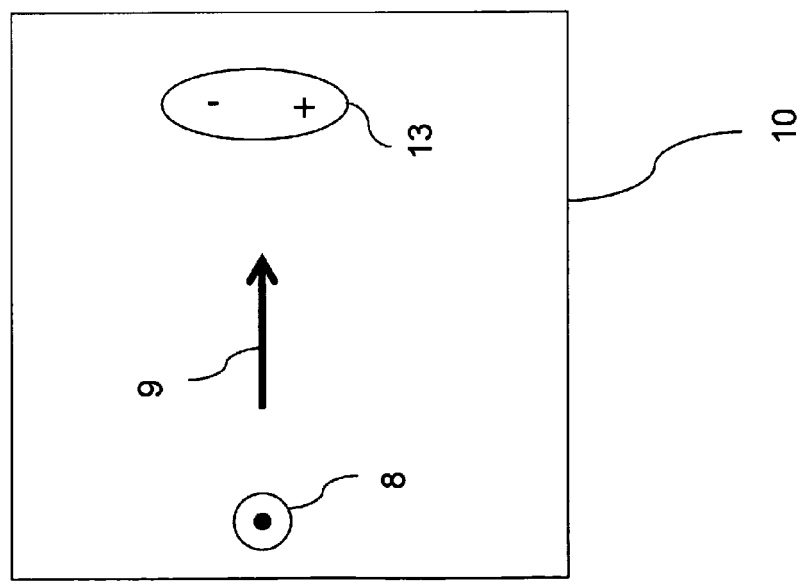

FIGS. 2a and 2b are schematic depictions showing two different settings in terms of positions of the illuminating light in the objective pupil.

As depicted in FIG. 2a, position 8 of the illuminating light, i.e. the relative position of the laser in the objective pupil, is at a "nine o'clock" azimuth. This correspondingly yields a propagation direction 9 of the evanescent field in terms of specimen 10 to be investigated, a dipole 13 being depicted for the sake of simplicity. FIG. 2a thus shows the relative position and the evanescent field resulting therefrom with its propagation direction 9 with respect to the orientation of dipole 13. It may be gathered that dipole 13 does not interact with a corresponding evanescent illumination, so that little or no fluorescent light intensity is detectable.

As depicted in FIG. 2b, position 11 of the laser light has changed, by comparison with what is depicted in FIG. 2a, from a nine o'clock to a twelve o'clock azimuth, resulting in a correspondingly modified propagation direction 12 of the evanescent field relative to specimen 10, or dipole 13, that is being investigated. It may be gathered that in this case an interaction with dipole 13 does take place, so that a certain fluorescent light intensity is detectable.

To avoid repetition, the reader is referred to the general portion of the description with regard to further features and descriptions of advantages.

In conclusion, be it noted very particularly that the exemplifying embodiment discussed above serves merely to describe the teaching claimed, but does not limit it to the exemplifying embodiment.

PARTS LIST

1 Interface (surface of specimen)
2 Incident laser light beam
3 Position (of laser light beam on/in interface)
4 Perpendicular (onto interface)
5 Reflected laser light beam
6 Arrow (symbolizing penetrating evanescent field)
7 Arrow (symbolizing propagation direction of evanescent field)
8 Position of illuminating light in objective pupil ("nine o'clock" azimuth)
9 Propagation direction of evanescent field (FIG. 2a)
10 Specimen
11 Position of illuminating light in objective pupil ("twelve o'clock" azimuth)
12 Propagation direction of evanescent field (FIG. 2b)
13 Dipole
α Angle between incident beam and perpendicular (FIG. 1)

What is claimed is:

1. A method of ascertaining the orientation of molecules in a biological specimen by total internal reflection, the method comprising:
   focusing illuminating light through an objective in different positions in a plane of a pupil of the objective so as to generate a plurality of respective differently oriented evanescent fields in the specimen; and
   correlating, with respective different orientations of molecules in the specimen, respective different fluorescence intensities resulting from the differently oriented evanescent fields,
   wherein the focusing illuminating light is performed so as to illuminate the specimen in evanescent fashion so as to generate a sequence of the differently oriented evanescent fields and respective images resulting from the fluorescence, and further comprising determining a respective first orientation of a first molecule based on a respective changing fluorescence intensity within the sequence.

2. The method as recited in claim 1 wherein the molecules are molecules of a cell.

3. The method as recited in claim 1 wherein the illuminating light includes light of a laser light source.

4. The method as recited in claim 1 wherein the focusing illuminating light is performed using an adjusting device configured to act two-dimensionally.

5. The method as recited in claim 4 wherein the focusing illuminating light is performed so as to illuminate a desired position.

6. The method as recited in claim 4 wherein the focusing illuminating light is performed so as to produce a first relative orientation of a first resulting evanescent field with reference to a first respective orientation of a first molecule orientation in accordance with a first different position.

7. The method as recited in claim 1 wherein the focusing illuminating light is performed so as to produce different respective interaction cross sections, based on different respective propagation directions of the evanescent fields relative to the respective different orientations of the molecules in the specimen, so as to produce the respective different fluorescence intensities.

8. The method as recited in claim 1 wherein the focusing illuminating light is performed so as to illuminate the specimen in evanescent fashion in a predetermined sequence of the different positions in the plane of the pupil of the objective.

9. The method as recited in claim 8 further comprising selecting the predetermined sequence of the different positions in the plane of the pupil of the objective so that the resulting differently oriented evanescent fields are oriented with respect to one another at predeterminable respective angles.

10. The method as recited in claim 9 wherein the selecting is performed so that the resulting differently oriented evanescent fields are oriented orthogonally with respect to one another.

11. A method of ascertaining the orientation of molecules in a biological specimen by total internal reflection, the method comprising:
    focusing illuminating light through an objective in different positions in a plane of a pupil of the objective so as to generate a plurality of respective differently oriented evanescent fields in the specimen;
    correlating, with respective different orientations of molecules in the specimen, respective different fluorescence intensities resulting from the differently oriented evanescent fields; and
    determining a respective first orientation of a first molecule based on an emission behavior of the first molecule in a context of first evanescent fields oriented differently with respect to the first molecule.

12. The method as recited in claim 11 wherein the first molecule includes a dipole.

13. The method as recited in claim 11 wherein the molecules are molecules of a cell.

14. The method as recited in claim 11 wherein the focusing illuminating light is performed using an adjusting device configured to act two-dimensionally.

15. The method as recited in claim 14 wherein the focusing illuminating light is performed so as to illuminate a desired position.

16. The method as recited in claim 14 wherein the focusing illuminating light is performed so as to produce a first relative orientation of a first resulting evanescent field with reference to a first respective orientation of a first molecule orientation in accordance with a first different position.

17. The method as recited in claim 11 wherein the focusing illuminating light is performed so as to produce different respective interaction cross sections, based on different respective propagation directions of the evanescent fields relative to the respective different orientations of the molecules in the specimen, so as to produce the respective different fluorescence intensities.

18. The method as recited in claim 11 wherein the focusing illuminating light is performed so as to illuminate the specimen in evanescent fashion in a predetermined sequence of the different positions in the plane of the pupil of the objective.

19. The method as recited in claim 18 further comprising selecting the predetermined sequence of the different positions in the plane of the pupil of the objective so that the resulting differently oriented evanescent fields are oriented with respect to one another at predeterminable respective angles.

20. The method as recited in claim 19 wherein the selecting is performed so that the resulting differently oriented evanescent fields are oriented orthogonally with respect to one another.

* * * * *